(12) United States Patent
Chen et al.

(10) Patent No.: US 7,679,748 B2
(45) Date of Patent: Mar. 16, 2010

(54) COUPLED WAVEGUIDE-SURFACE PLASMON RESONANCE BIOSENSOR

(75) Inventors: Shean-Jen Chen, Tainan (TW);
Yen-Chieh Mao, Kaohsiung (TW);
Jeng-Nan Yih, Zhubei (TW);
Fan-Ching Chien, Taoyuan (TW);
Chun-Yu Lin, Shalu Town (TW);
Yi-Ming Chu, Luzhu Shiang (TW);
Lai-Sheng Chen, Hsinchu (TW);
Wei-Han Wang, Xindian (TW);
Chao-Chi Wu, Kaohsiung (TW);
Yen-Chun Lin, Taipei (TW)

(73) Assignee: Industrial Technology Research Institute, Hsin-Chu (TW)

( * ) Notice: Subject to any disclaimer, the term of this patent is extended or adjusted under 35 U.S.C. 154(b) by 519 days.

(21) Appl. No.: 11/448,098

(22) Filed: Jun. 7, 2006

(65) Prior Publication Data

US 2006/0238767 A1    Oct. 26, 2006

(30) Foreign Application Priority Data

Nov. 3, 2005    (TW) ............................... 94138559 A

(51) Int. Cl.
G01N 21/55    (2006.01)
(52) U.S. Cl. ...................................... 356/445; 356/317

(58) Field of Classification Search .................. 356/417, 356/311, 317–318, 445–448; 422/55, 57, 422/82.05, 82.11; 435/287.1–287.2, 288.7, 435/808; 436/164, 805; 250/458.1, 214 R, 250/461.2; 385/12, 10
See application file for complete search history.

(56) References Cited

U.S. PATENT DOCUMENTS

| 6,483,096 | B1 | 11/2002 | Kunz ........................... 250/214 |
| 7,070,987 | B2 | 7/2006 | Cunningham et al. ..... 435/287.1 |
| 2003/0068657 | A1 | 4/2003 | Lin .............................. 435/7.9 |
| 2008/0037022 | A1* | 2/2008 | Nishikawa et al. .......... 356/445 |

* cited by examiner

*Primary Examiner*—Gregory J Toatley, Jr.
*Assistant Examiner*—Tri T Ton
(74) *Attorney, Agent, or Firm*—WPAT., P. C.; Justin King

(57) ABSTRACT

The present invention discloses a coupled waveguide-surface plasmon resonance biosensor, comprising: a grating layer formed of a transparent material, the grating layer comprising a first periodic grating structure; a waveguide layer formed on the first periodic grating structure, the refractive index of the waveguide layer being larger than the refractive index of the grating layer; a plasmon resonance layer formed on the waveguide layer, capable of being optically excited to cause a plasmon resonance wave; and a ligand layer formed on the plasmon resonance layer; capable of being bound to react with receptors of a sample to be tested.

18 Claims, 7 Drawing Sheets

COUPLED WAVEGUIDE-SURFACE PLASMON RESONANCE BIOSENSOR

BACKGROUND OF THE INVENTION

1. Field of the Invention

The present invention generally relates to a biosensor and, more particularly, to a coupled waveguide-surface plasmon resonance biosensor using a grating and a metal material without labeling so as to detect bio-molecular interaction in real time.

2. Description of the Prior Art

In bio-molecular interaction analysis (BIA), bio-chips have attracted tremendous attention from genomics into proteomics. Bio-chips are used to detect genetic performance and bio-molecular messages. The current detection is done mainly by fluorescence detection. In fluorescence detection, problems related to complicated fluorescence tags, difficulty in molecule tags, inevitable fluorescence decay and unavailability in dynamics information of real-time interaction occur. Therefore, a label-free detecting method is required. In 1902, R. W. Wood discovered exceptional reflection gratings. Afterwards, theoretical reports and experiments on various grating structures such as guided-mode resonant sub-wavelength gratings were found in literature.

In United States Patent Application Doc. No. 20030068657, it is disclosed a label-free methods for performing assays using a colorimetric resonant reflectance optical biosensor. In this method, a grating is provided on a molecular detection platform for molecular implantation. Monochromatic light is generated after light passes the grating. A sample to be tested is disposed on the platform and is then illuminated by a white light beam. The wavelength of the incident light is changed after reflection because the molecules of the tested sample are bound to react with receptors on the grating. The change in wavelength can be detected by a spectrum analyzer so as to measure the thickness of the protein without using a probe for detecting fluorescence as well as radioactive tags. However, the reflectance spectrum exhibits a wide FWHM (full width at half magnitude) leading to a poor wavelength resolution so that detection in physiology concentration is unavailable.

Please refer to FIG. 1, which is a conventional waveguide-coupled biosensor disclosed in U.S. Pat. No. 6,483,096. In the biosensor 1 in FIG. 1, a sample 10 to be tested is provided on a grating structure G on a waveguide layer 11. The incident light 13 is coupled into the waveguide layer 11 by the grating structure G. The incoupled light 131 interacts with the substance, which emits fluorescent light 132 with a longer wavelength. The incoupled light 131 and the fluorescent light 132 are coupled out by the grating structure G such that the emitted outcoupled light 1311 is clearly separated from the exciting light 1321. Such a clear separation increases the signal-to-noise ratio of the sensor signal for molecular detection by using the tunable laser diode and the phase-locked loop (PLL) technique. However, the tunable laser diode provides a narrower range of wavelength and thus a high-precision goniometer is required so as to couple the incident light into the waveguide at a correct angle for resonance coupling.

Therefore, to overcome the aforementioned shortcomings, there is need in providing a high-precision waveguide-coupled biosensor so as to detect bio-molecular interaction in real time.

SUMMARY OF THE INVENTION

It is a primary object of the present invention to provide a coupled waveguide-surface plasmon resonance biosensor, serving as a platform for molecular interaction so as to detect bio-molecular interaction in real time without labeling.

It is a secondary object of the present invention to provide a coupled waveguide-surface plasmon resonance biosensor, using optically excited free charges on a metal surface to cause plasmon resonance so as to achieve sensitivity enhancement.

It is another object of the present invention to provide a coupled waveguide-surface plasmon resonance biosensor, using a grating with a thickness reduced to bio-molecular scale such that bio-molecules eliminate chip resonance to obtain a narrowed reflection resonance peak and achieve resolution improvement.

In order to achieve the foregoing object, the present invention provides a coupled waveguide-surface plasmon resonance biosensor, comprising: a grating layer formed of a transparent material, the grating layer comprising a first periodic grating structure; a waveguide layer formed on the first periodic grating structure, the refractive index of the waveguide layer being larger than the refractive index of the grating layer; a plasmon resonance layer formed on the waveguide layer, capable of being optically excited to cause a plasmon resonance wave; and a ligand layer formed on the plasmon resonance layer; capable of being bound to react with receptors of a sample to be tested.

Preferably, the plasmon resonance layer is a metal film.

Preferably, the metal film is formed of one material selected from a group including gold, platinum, silver and combination thereof.

Preferably, the metal film has a thickness within a range from 5 nm to 2 µm.

Preferably, the plasmon resonance layer is a metal particle layer formed of a mixture of a plurality of nano metal particles and a dielectric material.

Preferably, the metal particle layer has a thickness within a range from 5 nm to 2 µm.

Preferably, the plurality of nano metal particles are formed of one material selected from a group including gold, platinum, silver and combination thereof.

Preferably, each of the plurality of nano metal particles has a diameter within a range from 1 nm to 2 µm.

Preferably, the plasmon resonance layer further comprises: a metal film formed on the waveguide layer; and a metal particle layer formed on the metal film, the metal particle layer being formed of a mixture of a plurality of nano metal particles and a dielectric material.

Preferably, the metal film is formed of one material selected from a group including gold, platinum, silver and combination thereof.

Preferably, the metal film has a thickness within a range from 5 nm to 2 µm.

Preferably, the plurality of nano metal particles are formed of one material selected from a group including gold, platinum, silver and combination thereof.

Preferably, the metal particle layer has a thickness within a range from 5 nm to 2 µm.

Preferably, the each of the plurality of nano metal particles has a diameter within a range from 1 nm to 2 µm.

Preferably, the coupled waveguide-surface plasmon resonance biosensor further comprises a self assembly monolayer formed between the ligand layer and the plasmon resonance layer.

Preferably, the self assembly monolayer is formed of one material selected from a group including sulfhydryl (HS), amine ($NH_2$), aldehyde (CHO), carboxyl (COOH), biotin and combination thereof.

Preferably, the waveguide layer is formed of one material selected from a group including sulfhydryl (HS), amine ($NH_2$), aldehyde (CHO), carboxyl (COOH), biotin and combination thereof.

Preferably, the waveguide layer is formed of one material selected from a group including silicon nitride, gallium nitride, tantalum oxide, indium tin oxide, indium gallium arsenide, gallium arsenide, indium phosphide, gallium arsenide antimonide, magnesium fluoride, zinc sulfide, zinc telluride, beryllium zinc telluride, magnesium selenide, aluminum gallium nitride, gold, platinum, silver, dielectric and combination thereof.

Preferably, the first periodic grating structure has a depth and a line-width both within a range from 50 nm to 2 µm.

Preferably, the waveguide layer has a thickness within a range from 5 nm to 2 µm.

BRIEF DESCRIPTION OF THE DRAWINGS

The objects, spirits and advantages of the preferred embodiments of the present invention will be readily understood by the accompanying drawings and detailed descriptions, wherein.

DETAILED DESCRIPTION OF THE PREFERRED EMBODIMENT

The present invention providing a coupled waveguide-surface plasmon resonance biosensor can be exemplified by the preferred embodiments as described hereinafter.

Coupled waveguide-surface plasmon resonance indicates that surface plasma are excited only at a small range of wavelength or by monochromatic light at a specific incident angles. The wavelength and the angle are referred to as the coupled waveguide-surface plasmon resonance wavelength and the coupled waveguide-surface plasmon resonance angle, respectively. When the coupled waveguide-surface plasmon resonance structure is disturbed by, for example, the minimal change of reflection index or thickness caused by bio-molecular absorption on the surface, the wave vector of the coupled surface plasma changes to cause variation of the resonance wavelength or the resonance angle. Therefore, bio-molecular interaction can be detected dynamically without labeling. Such a coupled waveguide-surface plasmon resonance structure having a grating exhibits excellent sensitivity in bio-molecular detection and is suitable for public health purpose or home use.

Surface plasmon resonance occurs as free charges on the metal surface disturbed by an applied magnetic field to cause coherent longitudinal resonance and travels as an electromagnetic wave along the surface. The surface plasmon resonance phenomenon can be detected by the reflection spectrum of coupled excited light through a prism or a grating. When the incident light matches the surface plasmon wave vector and causes surface plasmon resonance, the reflection in the reflection spectrum is minimal and the resonance phenomenon changes dramatically due to minimal change on the metal surface. Accordingly, the coupled waveguide-surface plasmon resonance biosensor is used to detect the minimal change of bio-molecules on the interface (for example, the dielectric constant and film thickness of the bio-molecules) caused by interactions of the bio-molecules at the interface of metal and liquid or gas.

The design of bio-chips focuses on the sensitivity of resonance of the optical waveguide being disturbed. And also, enhancement of detection resolution replies on a narrower reflection resonance peak. With a thinned grating waveguide, the narrower reflection resonance peak can be obtained. When the grating is thinned to a bio-molecular scale, the resonance phenomenon is easily disturbed by the bio-molecules. Therefore, in the present invention, the grating is designed to be thin and rigorous electromagnetic theory is applied to simulate the optical characteristics of a sub-wavelength grating so as to determine calculate the reflectivity, transmissivity, and diffractivity of vertical incident light.

Figure 1:
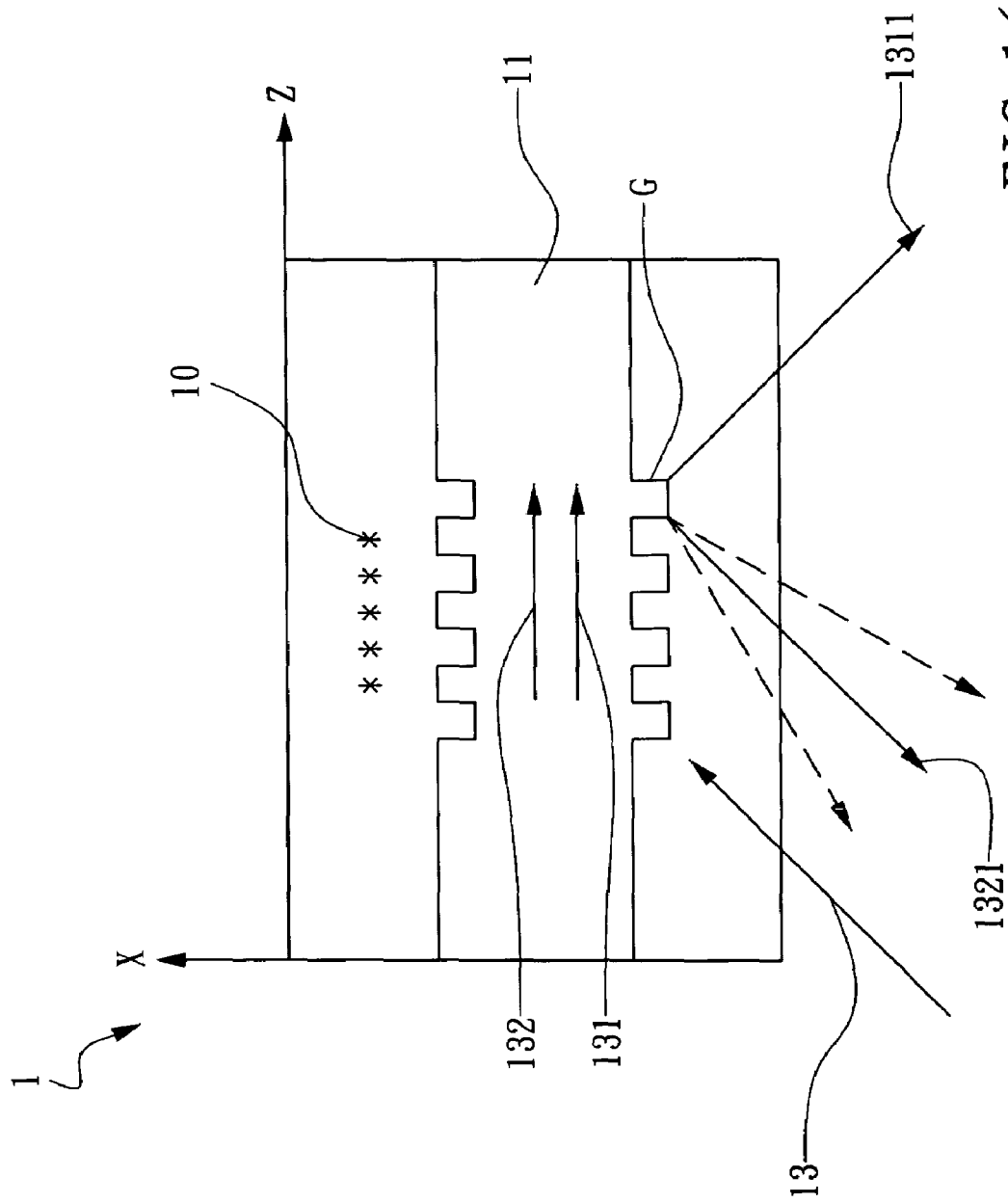
FIG. 1 is a schematic diagram showing a conventional waveguide-coupled biosensor in the prior art.
Figure 2A:
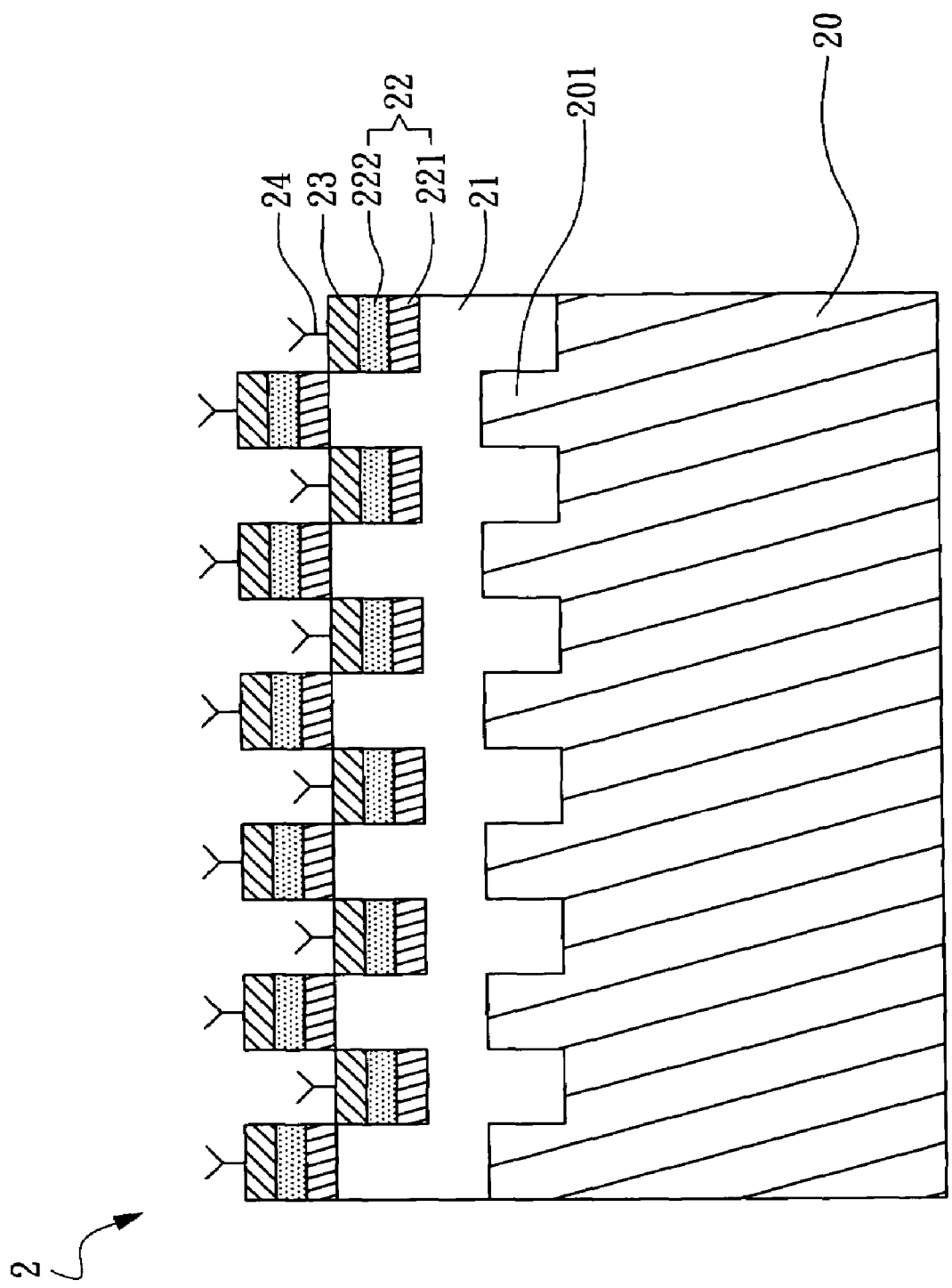
FIG. 2A is a cross-sectional view of a coupled waveguide-surface plasmon resonance biosensor according to the preferred embodiment of the present invention.
Figure 2B:
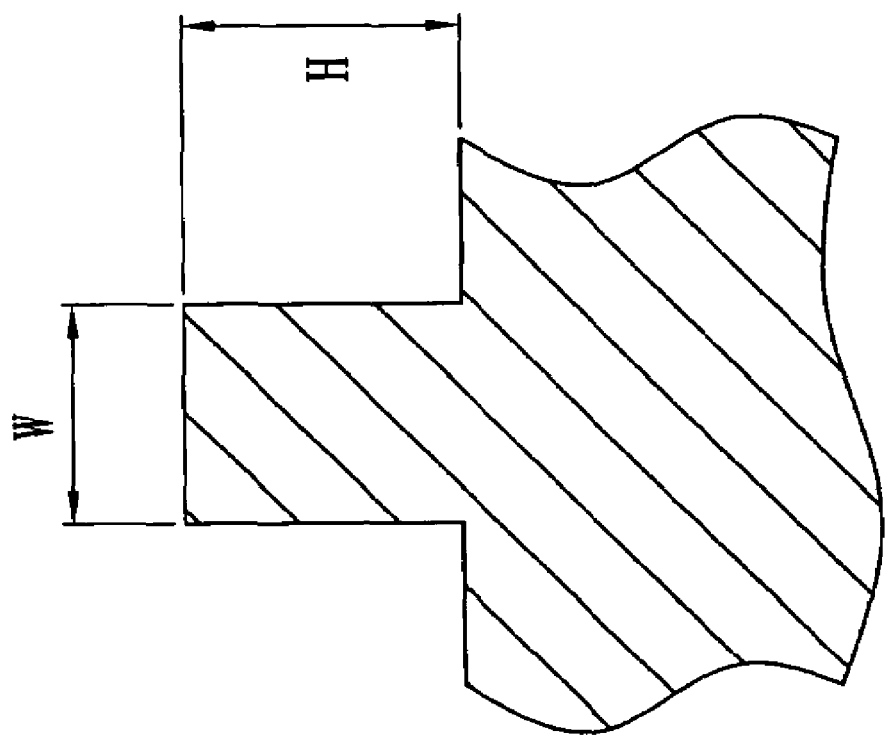
FIG. 2B is a schematic diagram showing a grating structure of the coupled waveguide-surface plasmon resonance biosensor according to the present invention.

Please refer to FIG. 2A, which is a cross-sectional view of a coupled waveguide-surface plasmon resonance biosensor according to the preferred embodiment of the present invention. The coupled waveguide-surface plasmon resonance biosensor 2 comprises a grating layer 20, a waveguide layer 21, a plasmon resonance layer 22 and a ligand layer 24. The grating layer 20 is formed of a transparent material and comprises a first periodic grating structure 201. The waveguide layer 21 is formed on the first periodic grating structure 201. The refractive index of the waveguide layer 21 is larger than the refractive index of the grating layer 20. The depth H and the width W of the first periodic grating structure 201 are within the range from 50 nm to 2 µm, as shown in FIG. 2B. In the present embodiment, the thickness of the waveguide layer 21 is within the range from 5 nm to 2 µm.

In the present embodiment, the grating layer 20 is a substrate, and the first periodic grating structure 201 is formed on the surface of the substrate. The substrate is formed of a transparent material such as quartz and glass, and is then etched or impressed to form a periodic concave-convex structure 201 on the substrate surface. The waveguide layer 21 is thus formed on the periodic concave-convex structure 201 using sputtering, deposition, and impressing. The refraction index of the waveguide layer 21 is larger than that of the neighboring regions. The waveguide layer 21 is formed of one material selected from a group including silicon nitride, gallium nitride, tantalum oxide, indium tin oxide, indium gallium arsenide, gallium arsenide, indium phosphide, gallium arsenide antimonide, magnesium fluoride, zinc sulfide, zinc telluride, beryllium zinc telluride, magnesium selenide, aluminum gallium nitride, gold, platinum, silver, dielectric and combination thereof. Alternatively, the waveguide layer 21 is formed of one material selected from a group including sulfhydryl (HS), amine ($NH_2$), aldehyde (CHO), carboxyl (COOH), biotin and combination thereof.

The plasmon resonance layer 22 is formed on the waveguide layer 21. The plasmon resonance layer 22 is capable of being optically excited to cause a plasmon resonance wave. The plasmon resonance layer 22 is formed of a metal film, a metal particle layer or combination thereof. In the present embodiment, the plasmon resonance layer 22 comprises a metal film 221 formed on the waveguide layer 21. On the metal film 221 is formed a metal particle layer 222 formed of a mixture of a plurality of nano metal particles and a dielectric material so as to enhance electromagnetic radiation and hence the sensitivity of surface plasmon resonance. The metal film 221 has a thickness within the range from 5 nm to 2 μm. The metal particle layer 222 has a thickness within the range from 5 nm to 2 μm. Each of the plurality of nano metal particles has a diameter within a range from 1 nm to 2 μm. Moreover, the metal particles and the metal film are formed of one material selected from a group including gold, platinum, silver and combination thereof.

The ligand layer 24 is formed on the plasmon resonance layer 22. The ligand layer 24 is capable of being bound to react with receptors of a sample to be tested. In the present embodiment, the ligand layer 24 is determined by the sample to be tested. A self assembly monolayer 23 can be formed between the ligand layer 24 and the plasmon resonance layer 22 so as to locate the ligand layer 24. The self assembly monolayer is formed of one material selected from a group including sulfhydryl (HS), amine (NH$_2$), aldehyde (CHO), carboxyl (COOH), biotin and combination thereof.

Figure 3A:
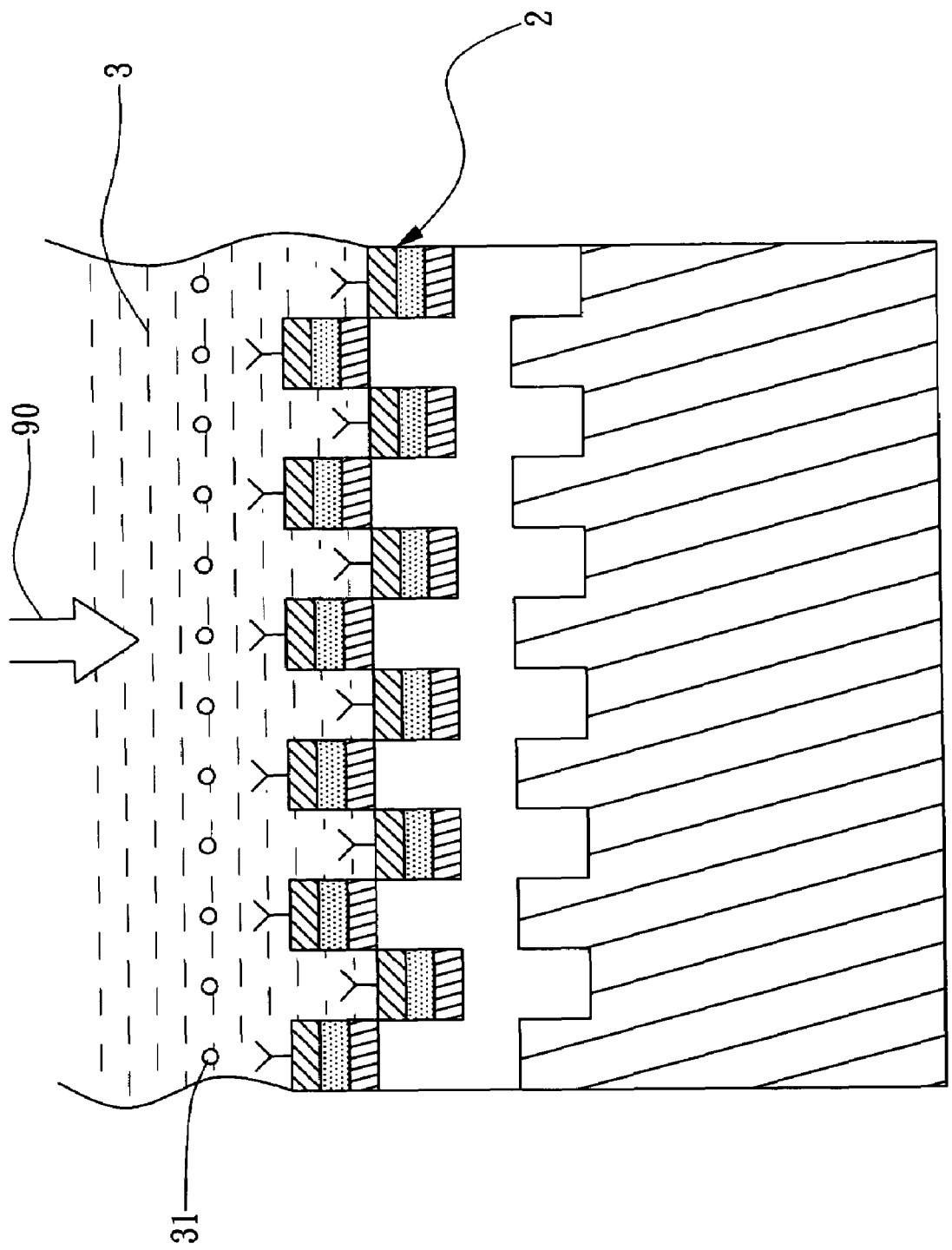
FIG. 3A is a cross-sectional view showing the coupled waveguide-surface plasmon resonance biosensor in use for detection according to the preferred embodiment of the present invention.

Please refer to FIG. 3A, which is a cross-sectional view showing the coupled waveguide-surface plasmon resonance biosensor in use for detection according to the preferred embodiment of the present invention. The structure shown in FIG. 2A is disposed in a medium 3 comprising receptors 31 to be tested so as to perform bio-detection. The medium 3 comprises water, alcohol or air. The incident light 90 is vertical or declined. Reflected light 91 is received and converted into a computer to determine the spectrum. The sensitivity of the coupled waveguide-surface plasmon resonance biosensor 2 is an order larger than that of a conventional sub-length grating waveguide biosensor.

Figure 3B:
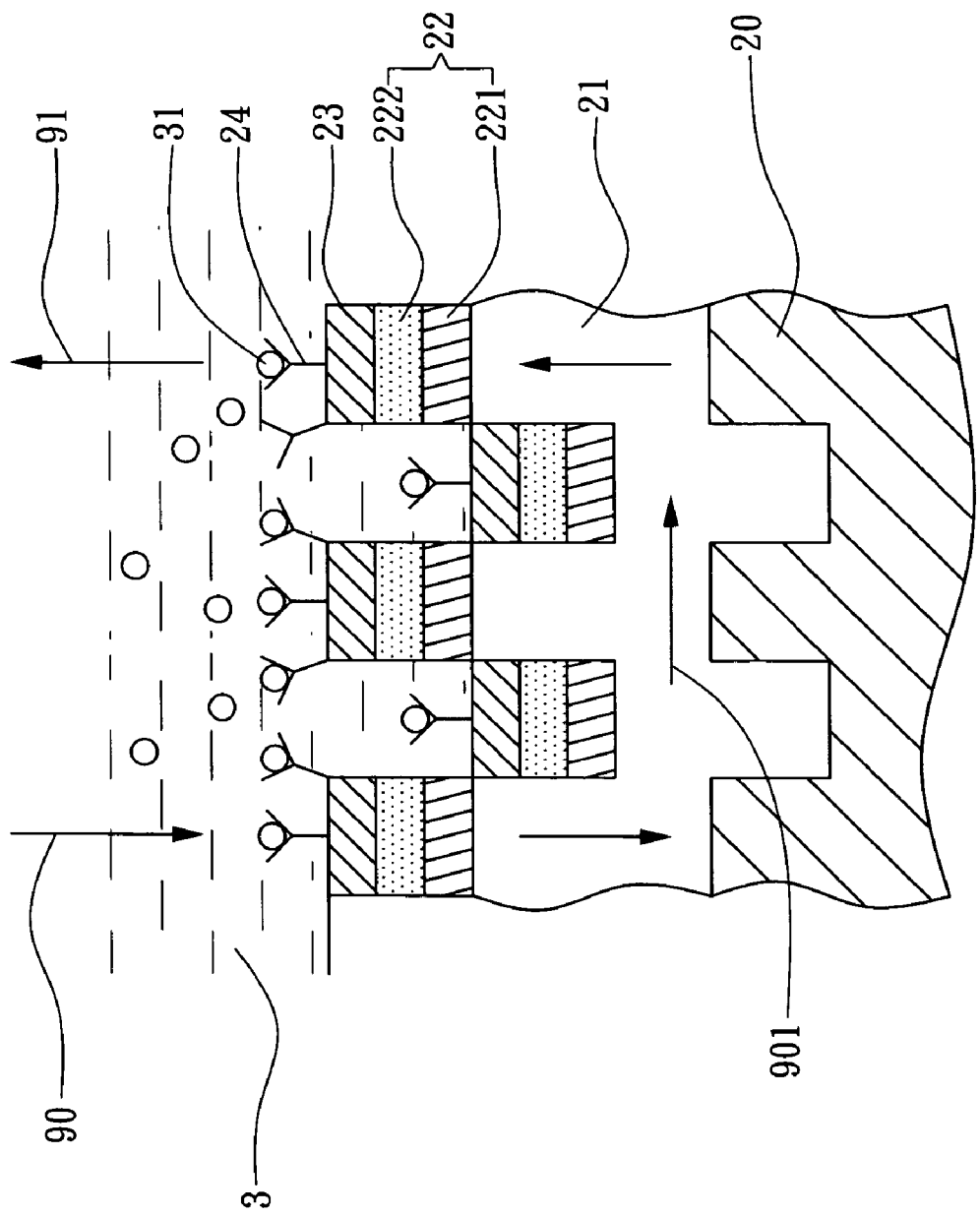
FIG. 3B is a cross-sectional view showing detection of tested molecules.
Figure 4A:
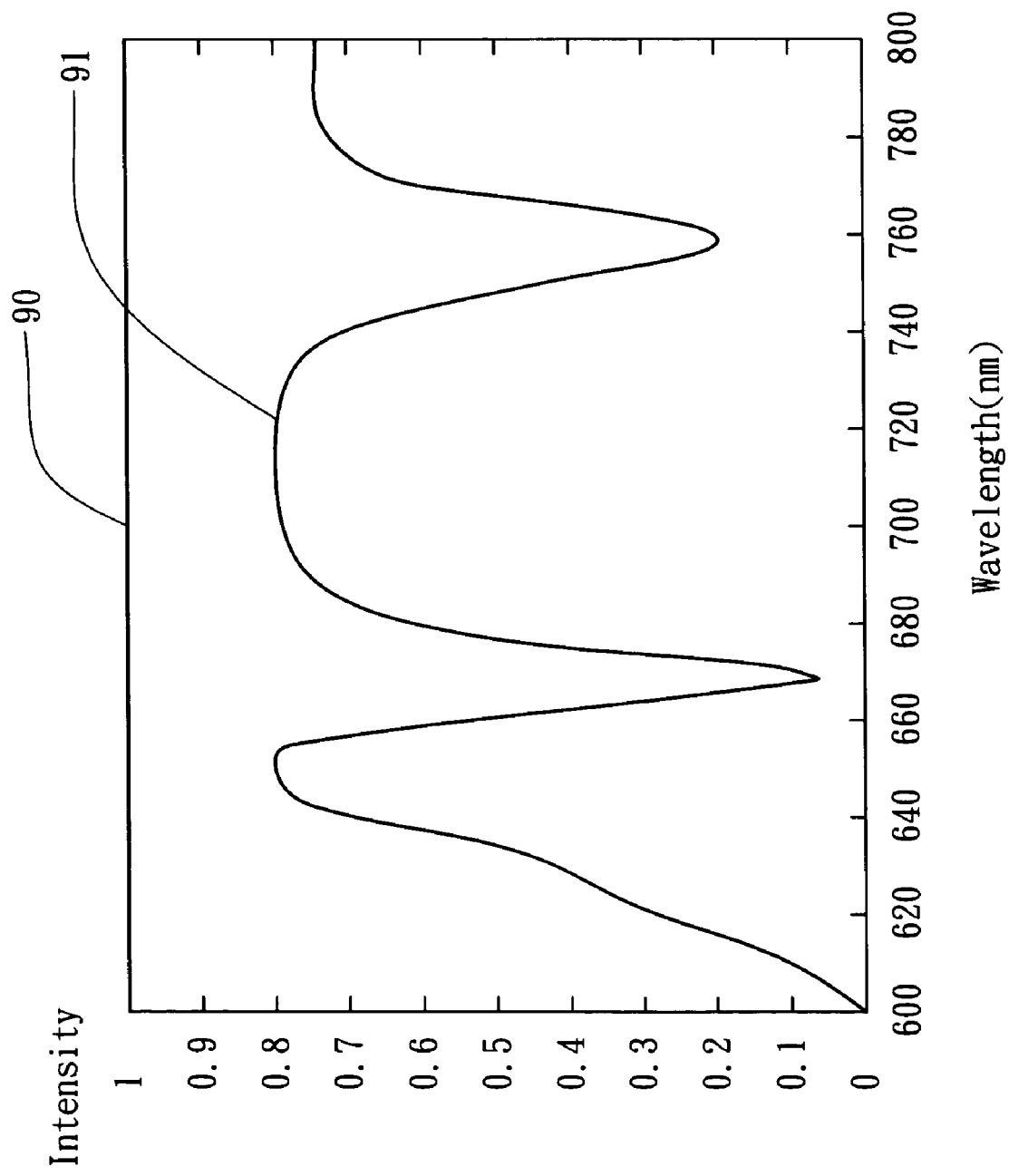
FIG. 4A and FIG. 4B are graphs showing zero-order reflection spectrum of tested molecules.
Figure 4B:
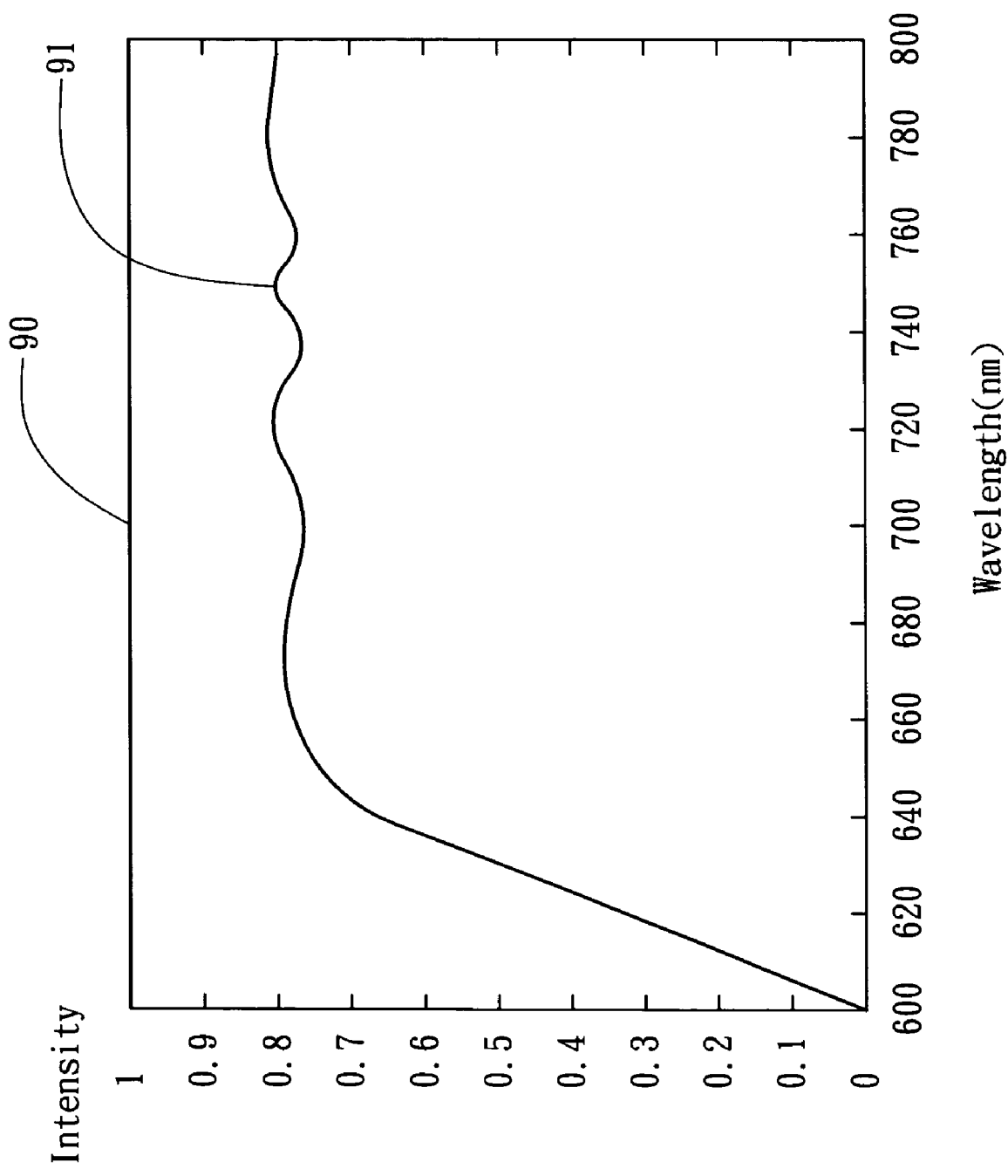

The ligand layer 24 on the biosensor 2 can only be combined with specific receptors. If the receptors 31 are predetermined objects, the receptors 31 will be combined with the ligand layer 24. Please also refer to FIG. 3B, if the receptors 31 in the medium 3 can be combined with the ligand layer 24 to absorb light at a certain wavelength, light attenuation is manifest as shown in FIG. 4A. Otherwise, if the receptors 31 cannot be combined with the ligand layer 24, the tested result is shown in FIG. 4B.

According to the above discussion, it is apparent that the present invention discloses a coupled waveguide-surface plasmon resonance biosensor, serving as a platform for molecular interaction so as to detect bio-molecular interaction in real time without labeling. Therefore, the present invention is novel, useful and non-obvious.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A coupled waveguide-surface plasmon resonance biosensor, comprising:
    a grating layer formed of a transparent material, said grating layer comprising a first periodic grating structure;
    a waveguide layer formed on said first periodic grating structure, the refractive index of said waveguide layer being larger than the refractive index of said grating layer;
    a plasmon resonance layer formed on said waveguide layer, capable of being optically excited to cause plasmon resonance wave; and
    a ligand layer formed on said plasmon resonance layer, capable of being bound to react with receptors of a sample to be tested.

2. The coupled waveguide-surface plasmon resonance biosensor as recited in claim 1, wherein said plasmon resonance layer is a metal film.

3. The coupled waveguide-surface plasmon resonance biosensor as recited in claim 2, wherein said metal film is formed of one material selected from a group including gold, platinum, silver and combination thereof.

4. The coupled waveguide-surface plasmon resonance biosensor as recited in claim 2, wherein said metal film has a thickness within a range from 5 nm to 2 μm.

5. The coupled waveguide-surface plasmon resonance biosensor as recited in claim 1, wherein said plasmon resonance layer is a metal particle layer formed of a mixture of a plurality of nano metal particles and a dielectric material.

6. The coupled waveguide-surface plasmon resonance biosensor as recited in claim 5, wherein said metal particle layer has a thickness within a range from 5 nm to 2 μm.

7. The coupled waveguide-surface plasmon resonance biosensor as recited in claim 5, wherein said plurality of nano metal particles are formed of one material selected from a group including gold, platinum, silver and combination thereof.

8. The coupled waveguide-surface plasmon resonance biosensor as recited in claim 5, wherein each of said plurality of nano metal particles has a diameter within a range from 1 nm to 2 μm.

9. The coupled waveguide-surface plasmon resonance biosensor as recited in claim 1, wherein said plasmon resonance layer, further comprising:
    a metal film formed on said waveguide layer; and
    a metal particle layer formed on said metal film, said metal particle layer being formed of a mixture of a plurality of nano metal particles and a dielectric material.

10. The coupled waveguide-surface plasmon resonance biosensor as recited in claim 9, wherein said metal film is formed of one material selected from a group including gold, platinum, silver and combination thereof.

11. The coupled waveguide-surface plasmon resonance biosensor as recited in claim 9, wherein said metal film has a thickness within a range from 5 nm to 2 μm.

12. The coupled waveguide-surface plasmon resonance biosensor as recited in claim 9, wherein said plurality of nano metal particles are formed of one material selected from a group including gold, platinum, silver and combination thereof.

13. The coupled waveguide-surface plasmon resonance biosensor as recited in claim 9, wherein said metal particle layer has a thickness within a range from 5 nm to 2 μm.

14. The coupled waveguide-surface plasmon resonance biosensor as recited in claim 1, further comprising a self assembly monolayer formed between said ligand layer and said plasmon resonance layer.

15. The coupled waveguide-surface plasmon resonance biosensor as recited in claim 14, wherein said self assembly monolayer is formed of one material selected from a group including sulfhydryl (HS), amine (NH$_2$), aldehyde (CHO), carboxyl (COOH), biotin and combination thereof.

16. The coupled waveguide-surface plasmon resonance biosensor as recited in claim 1, wherein said waveguide layer is formed of one material selected from a group including silicon nitride, gallium nitride, tantalum oxide, indium tin oxide, indium gallium arsenide, gallium arsenide, indium phosphide, gallium arsenide antimonide, magnesium fluoride, zinc sulfide, zinc telluride, beryllium zinc telluride, magnesium selenide, aluminum gallium nitride, dielectric and combination thereof.

17. The coupled waveguide-surface plasmon resonance biosensor as recited in claim 1, wherein said first periodic grating structure has a depth and a periodic width both within a range from 50 nm to 2 μm.

18. The coupled waveguide-surface plasmon resonance biosensor as recited in claim 16, wherein said waveguide layer has a thickness within a range from 5 nm to 2 μm.

* * * * *